(12) United States Patent
Erez et al.

(10) Patent No.: US 9,038,640 B2
(45) Date of Patent: May 26, 2015

(54) SYSTEM AND METHOD FOR FRACTIONAL TREATMENT OF SKIN

(75) Inventors: Danny Erez, Kfar Vitkin (IL); Gerard Tal, Petah-Tikva (IL)

(73) Assignee: Viora Ltd., Tel Aviv (IL)

( * ) Notice: Subject to any disclaimer, the term of this patent is extended or adjusted under 35 U.S.C. 154(b) by 227 days.

(21) Appl. No.: 13/435,297

(22) Filed: Mar. 30, 2012

(65) Prior Publication Data
US 2012/0253416 A1 Oct. 4, 2012

Related U.S. Application Data

(60) Provisional application No. 61/469,841, filed on Mar. 31, 2011.

(51) Int. Cl.
| A61B 19/00 | (2006.01) |
| A61F 7/00 | (2006.01) |
| A61B 18/14 | (2006.01) |
| A61H 9/00 | (2006.01) |
| A61B 18/20 | (2006.01) |
| A61B 18/00 | (2006.01) |

(52) U.S. Cl.
CPC .............. *A61B 18/14* (2013.01); *A61H 9/0057* (2013.01); *A61B 18/203* (2013.01); *A61B 2018/00047* (2013.01); *A61B 2018/0016* (2013.01); *A61B 2018/00291* (2013.01); *A61B 2018/00452* (2013.01); *A61B 2018/1467* (2013.01); *A61B 2019/465* (2013.01); *A61H 2201/0207* (2013.01); *A61H 2201/0214* (2013.01); *A61H 2201/0285* (2013.01); *A61H 2201/10* (2013.01); *A61H 2201/1695* (2013.01); *A61H 2201/5005* (2013.01); *A61H 2207/00* (2013.01)

(58) Field of Classification Search
CPC ........... A61B 2018/00452; A61B 2018/00476; A61B 2017/306; A61B 2017/308
USPC .................. 606/3, 8–16; 607/88–93, 96–112; 128/898
See application file for complete search history.

(56) References Cited

U.S. PATENT DOCUMENTS

| 5,735,844 | A | * | 4/1998 | Anderson et al. | 606/9 |
| 7,241,291 | B2 | * | 7/2007 | Kreindel et al. | 606/9 |
| 7,282,060 | B2 | * | 10/2007 | DeBenedictis et al. | 607/88 |
| 8,571,648 | B2 | * | 10/2013 | Anderson et al. | 604/20 |
| 2004/0034341 | A1 | * | 2/2004 | Altshuler et al. | 606/3 |
| 2006/0079947 | A1 | * | 4/2006 | Tankovich et al. | 607/89 |
| 2006/0276778 | A1 | * | 12/2006 | Sink | 606/9 |
| 2006/0287646 | A1 | * | 12/2006 | Altshuler et al. | 606/9 |
| 2007/0049996 | A1 | * | 3/2007 | Black | 607/89 |
| 2007/0118098 | A1 | * | 5/2007 | Tankovich | 606/9 |

* cited by examiner

*Primary Examiner* — Ahmed Farah
(74) *Attorney, Agent, or Firm* — Pearl Cohen Zedek Latzer Baratz LLP

(57) ABSTRACT

A system and method for treatment of skin including a treatment surface having numerous small energy emitting points for fractional skin treatment as well as negative pressure outlets. During a treatment, negative pressure from the outlets may exert a pulling force on an opposing tissue surface to bring the tissue into contact with the energy points.

4 Claims, 2 Drawing Sheets

SYSTEM AND METHOD FOR FRACTIONAL TREATMENT OF SKIN

CROSS REFERENCE TO RELATED APPLICATIONS

This application claims the benefit of U.S. Provisional Application No. 61/469,841, filed on Mar. 31, 2011, which is incorporated herein in its entirety.

FIELD OF THE INVENTION

This application relates to skin treatment, and particularly to treatment of skin with energy and application of negative pressure to the treated skin.

BACKGROUND OF THE INVENTION

The application of energy such as through lasers or bipolar radiofrequency (RF) for coagulation and ablation of soft tissues is known. RF may be applied as part of nonablative deep dermal heating treatment for skin tightening, body shaping and other therapies. Certain applications may apply RF energy to a relatively large area of soft tissue such as one to two square centimeters or more. Alternatively or in addition, several very small areas of tissue may be treated through the concurrent application of RF through a group of small electrodes which may be brought into contact with the tissue, in a process known as fractional treatment. The efficacy of fractional treatment may be reduced by incomplete contact between a target area of tissue and the numerous small electrodes through which RF energy is passed.

SUMMARY OF THE INVENTION

Embodiments of the invention may include a device or apparatus for treating skin or other tissues where the device includes a treatment surface that may be placed in contact with or proximate to a skin surface to be treated. The surface may include several or numerous outlets for exerting negative pressure from the surface of the device, as well as several or numerous energy emission points such as electrodes or lasers to transmit energy into the tissue. The pressure outlets may be distributed, interspersed or placed among the array of energy points so that negative pressure or suction from for example one or more of the outlets exerts a force to pull a portion of the opposing tissue surface into contact with an energy point that is near or in an area of the outlet. Negative pressure from a second outlet may likewise exert a force to pull another portion of the opposing tissue surface into contact with one or more of the other energy points that are in the area of such second outlet. In some embodiments, energy may be emitted from the energy points once the pressure has exerted the pulling force, and the opposing tissue has been brought close to or in contact with the energy points. In some embodiments, energy may be emitted from alternating energy points in the array of energy points so that some or a group of energy points is energized while others or another group of energy points are de-energized. In some embodiments, a device may include a cavity or receptacle to collect debris that may be loosened or released from the tissue during a treatment and the exertion of negative pressure. In some embodiments energy points may be positioned or distributed on the surface, at a density of from 10 to 100 points per square centimeter of the treatment surface. In some embodiments, energy may be emitted from the energy points at a level of approximately from 10 to 100 milliJoules per point.

In some embodiments, energy may be transmitted from energy points in pulses having a duration of from 0.05 second to 0.5 seconds. In some embodiments, energy emission points and outlets may be arranged in one or more arrays on the treatment surface, where outlets are arranged in an array and energy points are arranged in an array, and the two arrays overlap.

In some embodiments energy points may be from 100 microns to 1000 microns in diameter. In some embodiments a device or apparatus may include a thermo-electric cooling unit and a pressure sensor.

In some embodiments a controller may vary a level of energy emitted by one or more of the energy emission points.

Embodiments of the invention may include a method for treating tissue, where the method includes applying to such tissue a treatment surface having energy emission points and negative pressure outlets. The method may continue to exert a pulling force from the negative pressure outlets against the opposing tissue, so that the pulling force from a first outlet or group of outlets pulls a first area of the tissue into contact with one or more energy points, and the pulling force from a second outlet pulls a second area of tissue into contact with a second one or more energy points.

In some embodiments exerting the pulling force from the outlets may be performed concurrently with emission of energy from the energy points. In some embodiments, emission of energy may be delayed until a threshold level of negative pressure has been exerted and the tissue has come into contact with or in proximity of the energy points. Some embodiments may include capturing debris released from the tissue in a storage cavity behind the treatment surface. Some embodiments may include applying the treatment surface that has energy emission points interspersed among negative pressure outlets. In some embodiments, applying the treatment surface may include applying a treatment surface where the outlets and energy points are arranged in two arrays that overlap. In some embodiments, a first group of energy points may be energized before a second group or in alternating energizing periods. In some embodiments energy may be emitted in varying intensities and varying frequencies during a course of a single treatment or pulse of energy Some embodiments may include a device having a hardened surface with an array of electrodes and an array of negative pressure outlets, so that when negative pressure is released from the outlets, an opposing tissue surface is pulled into contact with the electrodes, and upon such pulling, the electrode emits energy into the opposing tissue.

BRIEF DESCRIPTION OF THE DRAWINGS

The subject matter regarded as the invention is particularly pointed out and distinctly claimed in the concluding portion of the specification. The invention, however, both as to organization and method of operation, together with features and advantages thereof, may best be understood by reference to the following detailed description when read with the accompanied drawings in which:

DETAILED DESCRIPTION OF EMBODIMENTS OF THE INVENTION

In the following description, various embodiments of the invention will be described. For purposes of explanation, specific examples are set forth in order to provide a thorough understanding of at least one embodiment of the invention. However, it will also be apparent to one skilled in the art that other embodiments of the invention are not limited to the examples described herein. Furthermore, well-known features may be omitted or simplified in order not to obscure embodiments of the invention described herein.

The term "skin treatment" as used in this document may refer to treatment of local defects that may be found in the skin. These may include cellulite treatment, skin tightening, body contouring skin brightening, reduction of hyperpigmentation, improved skin texture, scar reduction, wrinkle smoothing and other treatments of other conditions.

Figure 1:
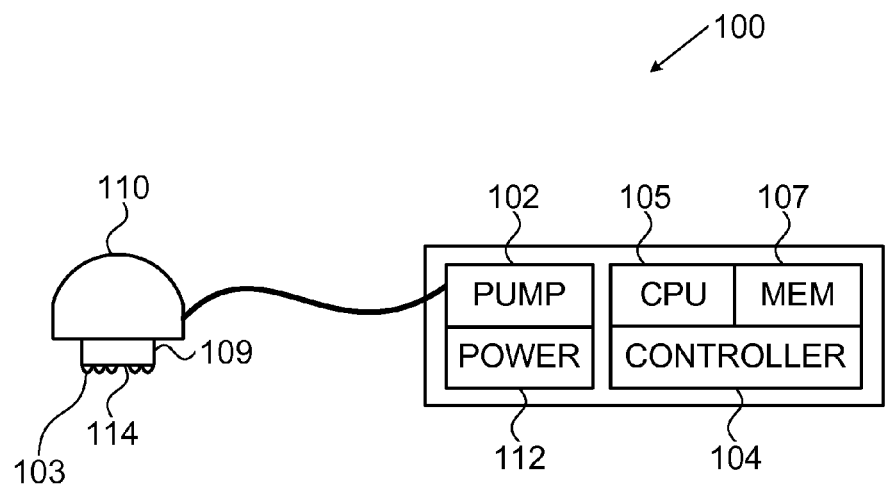
FIG. 1 is a schematic representation of a skin treatment system according to embodiments of the invention.

Reference is made to FIG. 1, a schematic representation of a skin treatment system according to embodiments of the invention. In some embodiments, a skin treatment system 100 may be used to treat aesthetic conditions such as wrinkled skin, hyperpigmentation and for body shaping. Other uses or benefits may occur in other embodiments. In some embodiments, the skin treatment may involve treating subcutaneous adipose tissue. Skin treatment system 100 may include a negative pressure device 102 and a plurality of RF electrodes 103, lasers or other energy emitting points. In some embodiments, energy emitting points are described as electrodes but other types of energy emitting points may be used such as light emitters, heat emitters, laser energy emitters, or emitters of other electro-magnetic radiation, or other energy forms. When used herein, negative pressure may include for example a vacuum or suction.

System 100 may further be connected to a controller 104 that may include a processor 105 and a memory 107. Controller 104 may be set to vary or control a frequency at which energy emission points such as electrodes 103, to vary a time or duration of such emission of energy, to vary a strength of negative pressure, or for varying other parameters of operation of system 100. System 100 may include an applicator 109 that may be in or on a housing 110 that may be portably or detachably connected to controller 104, a power or energy source 112, and negative pressure device 102 such as a pump. A distal end of applicator 109 may include a surface 114 that may be held against a tissue surface and that may include a plate or treatment surface having dimensions of approximately 10 mm by 15 cm. Other sizes and dimensions may be used.

In some embodiments, system 100 may include a fan to cool certain heat emitting components, such as a thermoelectric cooling device.

Figure 2:
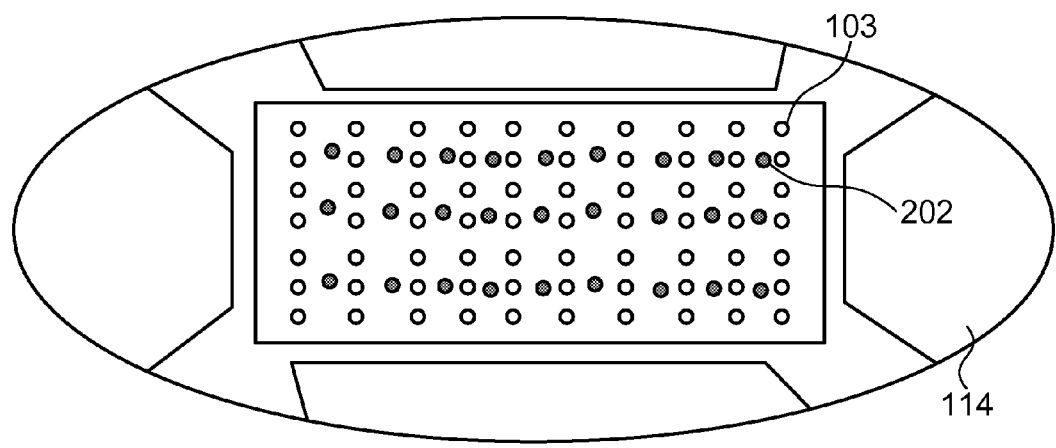
FIG. 2 is a schematic view of a surface of an applicator showing electrodes and negative pressure outlets in accordance with an embodiment of the invention.

Reference is made to FIG. 2, a schematic view of a surface of an applicator showing electrodes and negative pressure outlets in accordance with an embodiment of the invention. Surface 114 may be square, rectangular, round, oval or another convenient shape. Surface 114 is preferably fashioned of plastic may be include metals or ceramic. Surface 114 should be sufficiently hardened to withstand both the heat or other energy delivered from electrodes 103 that appear on surface 114, and to withstand the exertion of a pulling force from negative pressure outlets 202 that may end on surface 114. Surface 114 may include a series, pattern, array or other arrangement of treatment points, electrodes 103 or other energy emitters each of which may direct energy into a tissue or skin. Surface 114 may also include a series, array or pattern of several negative pressure outlets 202. Outlets 202 may be interspersed with, proximate to, scattered among or otherwise arranged so that they are close to one or more electrodes 103. In FIG. 2, outlets 202 are arranged in rows and columns that are between or intersect rows and columns of electrodes 103. Other arrangements of electrodes 103 and outlets 202 are possible, such as for example in overlapping arrays of columns and rows, in concentric or overlapping circles or ovals, or in other shapes or configurations where the negative pressure from an outlet or a number of outlets is sufficient to pull a portion of tissue into contact with one or more of its neighboring or nearby electrodes 103.

Figure 3:
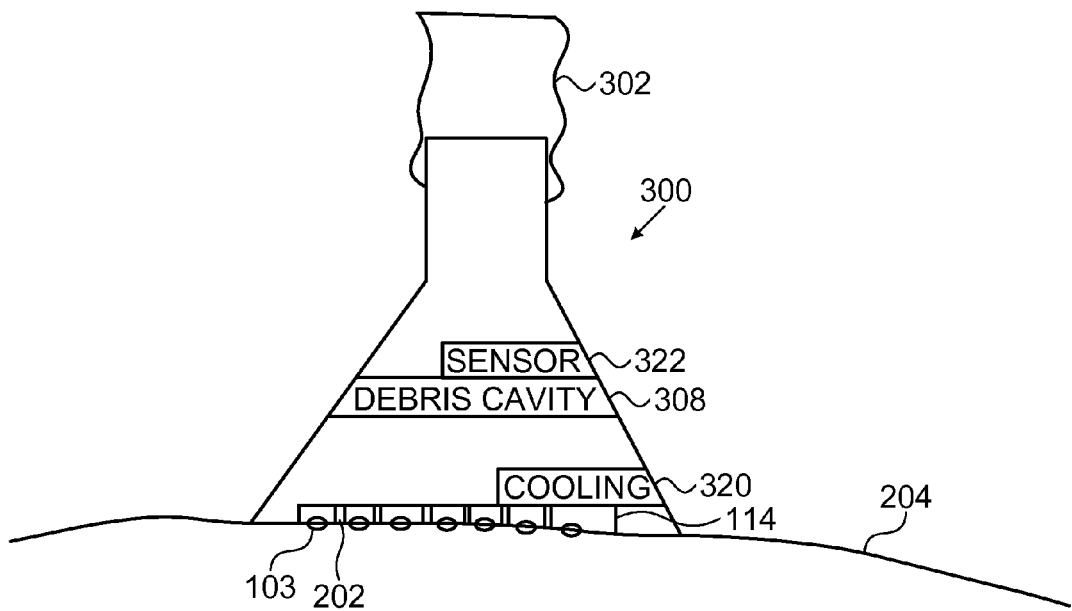
FIG. 3 is a schematic view of an applicator on a skin surface in accordance with an embodiment of the invention.

In operation, during a treatment of tissue by system 100, energy may be emitted by several or all of electrodes 103, and negative pressure may be concurrently, or at the same time, or substantially at the same time or during a period when such negative pressure is applied through outlets 202. Negative pressure from outlets 202 may exert a pulling force against an opposing surface such as the skin or tissue which is the subject of the treatment. Such pulling force may pull portions of the opposing surface 204 (as is shown in FIG. 3), such as the skin, into close contact with electrodes 103. Such negative pressure may also provide therapeutic benefit to the area of tissue being treated, as is known in the field. In some embodiments, the concurrent and simultaneous treatment through (i) the fractional delivery of energy by way of numerous small electrodes 103 for deep dermal heating, (ii) the increased contact of portions of tissue with electrodes 103, and (iii) the therapeutic benefit of negative pressure on the tissue that may result in an effective treatment of the subject tissue. In some embodiments less than all three of such of the aforesaid functions or processes may be achieved or provided concurrently or at all. For example, a level of negative pressure from outlets may not be sufficient to achieve therapeutic benefits for the tissue, but may be sufficient to increase or secure a contact an electrode 103 with an opposing tissue surface 204. In some embodiments, an application of negative pressure may be extended beyond a period of an emission of energy from electrodes 103. In some embodiments an application of energy from electrodes 103 may extend beyond an application of negative pressure. Other pre-defined sequences of energy and negative pressure may be used. For example, electrodes may be directed to release or emit energy only once a pressure has been built up between tissue surface 204 and one or more electrodes 103 so that tissue surface 204 is in contact with electrode 103 during the emission of energy. In some embodiments, a build up of pressure on tissue surface 204 may increase a blood flow to an area of such surface 204.

Reference is made to FIG. 3, a schematic side view of an applicator on a skin surface in accordance with an embodiment of the invention. Housing 300 may be connected to a hose 302 or other conveyor of negative pressure, and such negative pressure may be conducted to outlets 202. Treatment points such as electrodes 103 may be interspersed or arranged among and proximate to outlets 202 so that negative pressure may draw a portion of opposing skin surface 204 into close contact with electrodes 103. Housing 300 may also contain conduits for power transmission and control functions to electrodes 103.

In some embodiments, surface 114 may include a matrix or pattern of numerous electrodes such as 10 or 12 rows and 12 columns for a surface of 10 mm by 15 mm, and an effective treatment area of approximately 13 mm×13 mm. Within such a pattern, there may be included 30 to 40 negative pressure outlets 202 arranged or interspersed among the electrodes 103. Other densities of electrodes 103 and outlets 202 may be used. In some embodiments, electrodes 103 may be approximately 100 to 1,000 microns in diameter and may emit RF energy at a frequency of 1 MHz, or within a frequency range of 0.2 MHz to 20 Mhz, with pulses of 0.05-0.5 sec and total energy of from 10 to 100 mj/pin and with a density of from 10 to 100 electrodes per square centimeter. Other frequencies, pulse durations and energy levels are possible. Use of several or multiple frequencies in pulse sequences are also possible as is varying a level of energy emitted and/or a frequency of energy emitted by one or more electrodes 103 in one or more pulses. Such frequencies may be varied in a pre-defined sequence or time pattern of administration in one or more pulses or in a randomized sequence or time patter in one or more pulses, or in a combination thereof. In some embodiments, energy at two, several or multiple frequencies may be emitted from electrodes at a pre-defined (such as within one pulse) or randomized time pattern within one or more pulses or treatments. In some embodiments energy levels may be kept low to create minor and controlled damage to small areas of tissue that triggers a healing process with low impact. Such process may also promote enhanced local blood flow and collagen formation.

In some embodiments, a negative pressure exerted through outlets 202 may be in a range of 0.72-4.35 pound per square inch (PSI). Other pressures may be used. In some embodiments, a thermo-electric cooler 320 may be added to surface 114 to cool one or both of surface 114 and an opposing tissue or skin, and a pressure sensor 322 may be added to monitor a pressure exerted on a tissue surface. In some embodiments electrodes 103 may be energized or directed to emit energy at varying intervals to provide short bursts of energy. In some embodiments, a single electrode 103, groups of electrodes 103 such as a row or column or other arrangement may be selected by a controller for alternating an energizing of electrodes so that a first group of electrodes such as a row or column of electrodes may be energized while, during, before or after a remainder or second group is de-energized.

In some embodiments, a build up of pressure caused by a closing of one or more outlets 202 resulting from contact of surface 114 and tissue surface 204 may be detected by sensor 322. Such build up may be an indication of close contact between tissue surface 204 and surface 114 (and hence contact between tissue surface 204 and electrodes 103). Such detected pressure may be used as a trigger for an emission of energy from electrodes 103 or energy emission points, and controller 104 may in response to such detected pressure issue a signal to one or more electrodes 103 to emit energy into tissue surface 204.

In some embodiments, a space, container or cavity 308 inside of housing 300 and behind or distal from surface 114 such that the cavity is located in housing 109 somewhere between surface 114 and a connection of housing 110 to hose 302. Cavity 308 may collect and temporarily store skin or tissue fragments, debris and other materials that may be dislodged from a treated area during a treatment.

Figure 4:
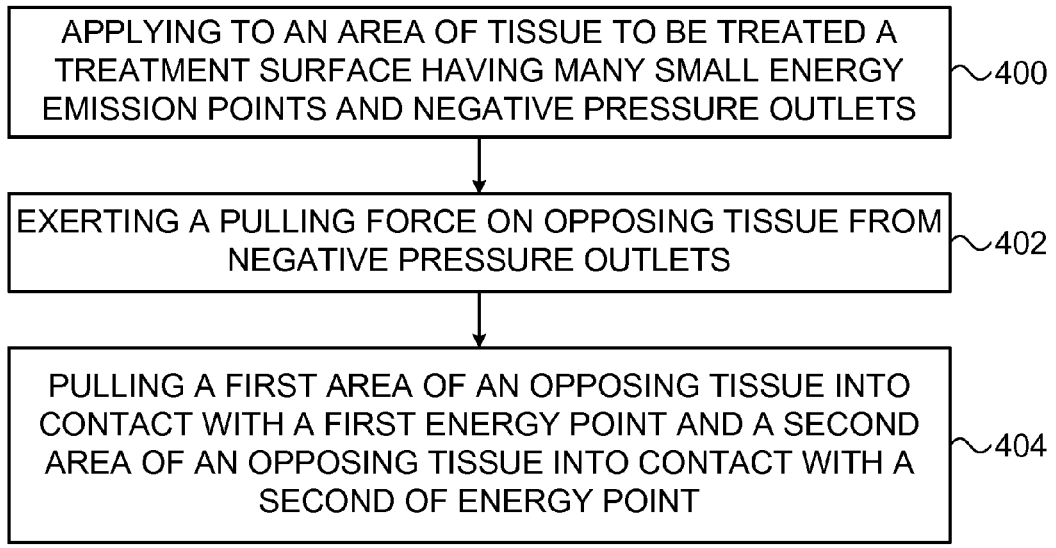
FIG. 4 is a flow diagram of a method in accordance with an embodiment of the invention.

Reference is made to FIG. 4, a flow diagram of a method in accordance with an embodiment of the invention. In block 400 a treatment surface of a device may be applied to an area of tissue to be treated. The treatment surface may include many small electrodes or other energy emission points, as well as many (though possibly fewer) negative pressure outlets. In block 402, negative pressure conducted from the outlets may exert a pulling force on tissue to which the surface is applied or which opposes the treatment surface. In block 404, the pulling force from a first outlet may pull a first part of the tissue being treated into contact with a first energy point, and the pulling force from a second of the outlets may pull a second area of the tissue into contact with a second of the energy points.

In some embodiments, energy is emitted by an energy point only upon a contact of an opposing surface such as a tissue or skin, with an energy point.

In some embodiments, energy is emitted from the energy points only when a negative pressure is released from the outlets.

Some embodiments may include capturing in a storage cavity behind the treatment surface, to store debris released from tissue by the negative pressure.

In some embodiments, the energy points may be arranged in an array of rows, columns, circles or other shapes and configurations, and the outlets may be interspersed or arrange in an overlapping array among the energy points. In some embodiments, energy points may have a density of from 50 to 75 points per square centimeter on the treatment surface. In some embodiments, approximately 62 milliJoules may be emitted from each energy point or some other range of from 10 to 100 milliJoules may be used, and an RF frequency of 1 MHz may be used.

While the invention has been described with respect to a limited number of embodiments, it will be appreciated by persons skilled in the art that the present invention is not limited by what has been particularly shown and described herein. Rather the scope of the present invention includes both combinations and sub-combinations of the various features described herein, as well as variations and modifications which would occur to persons skilled in the art upon reading the specification and which are not in the prior art.

We claim:

1. A method of treating human tissue, comprising:
   applying a treatment surface to said tissue, said surface including a plurality of energy emission points and a plurality of negative pressure outlets;
   exerting a pulling force from said negative pressure outlets against a tissue opposing said treatment surface; and
   energizing a first group of said plurality of energy emission points before an energizing of a second group of said plurality of energy emission points;
   wherein said pulling force from a first of said plurality of outlets pulls a first area of said tissue into contact with a first of said energy emission points, and said pulling force from a second of said plurality of outlets pulls a second area of said tissue into contact with a second of said energy emission points;
   wherein the energy emission points have a diameter in the range of 100 microns to 1000 microns, to allow fractional treatment of the tissue and wherein said plurality of energy emission points are interspersed among said plurality of negative pressure outlets and said plurality of energy emission points are arranged in a first array on said surface and said plurality of said outlets are arranged in a second array on said surface, said first array overlapping said second array.

2. The method as in claim 1, comprising exerting said pulling force from said plurality of outlets, said pulling concurrently with emission of energy from said energy emission points.

3. The method as in claim 1, comprising capturing in a storage cavity behind said surface, debris released from said tissue by said negative pressure.

4. The method as in claim 1, comprising varying in a pulse, a level of energy emitted by a first group of said plurality of energy emission points.

\* \* \* \* \*